United States Patent [19]

Fuchs et al.

[11] Patent Number: 5,757,482
[45] Date of Patent: May 26, 1998

[54] MODULE FOR OPTICAL DETECTION IN MICROSCALE FLUIDIC ANALYSES

[75] Inventors: Martin Fuchs, Uxbridge; Lance Bryant Koutny, Framingham, both of Mass.

[73] Assignee: PerSeptive Biosystems, Inc., Framingham, Mass.

[21] Appl. No.: 425,290

[22] Filed: Apr. 20, 1995

[51] Int. Cl.$^6$ .................. G01N 21/03; G01N 21/05
[52] U.S. Cl. .................. 356/246; 356/410; 356/440
[58] Field of Search .................. 356/246, 440, 356/410

[56] References Cited

U.S. PATENT DOCUMENTS

| | | | |
|---|---|---|---|
| 4,823,168 | 4/1989 | Kamahori et al. | 356/246 |
| 5,006,210 | 4/1991 | Yueng et al. | 204/180.1 |
| 5,057,216 | 10/1991 | Chervet | 210/198.2 |
| 5,061,361 | 10/1991 | Gordon | 209/299 R |
| 5,092,973 | 3/1992 | Zare et al. | 204/182.1 |
| 5,141,548 | 8/1992 | Chervet | 65/108 |
| 5,194,915 | 3/1993 | Gilby | 356/318 |
| 5,228,969 | 7/1993 | Hernandez | 204/299 R |
| 5,235,409 | 8/1993 | Burgi et al. | 356/436 |
| 5,273,633 | 12/1993 | Wang | 204/180.1 |
| 5,303,021 | 4/1994 | Kita | 356/72 |
| 5,318,686 | 6/1994 | Dill et al. | 204/299 R |
| 5,326,973 | 7/1994 | Eckerbom et al. | 356/440 X |
| 5,493,405 | 2/1996 | Holme | 356/440 |

FOREIGN PATENT DOCUMENTS 0 616 211 A1   9/1994   European Pat. Off. .

OTHER PUBLICATIONS

Sobek et al "A Microfabricated Flow Chamber for Optical Measurements in Fluids". Proceedings of IEEE Micro Electro Mechanical Systems, Fort Lauderdale, Fl, Feb. 7, 1993, pp. 219–224.

Mesaros et al., "Continuous Electrophoretic Separations in Narrow Channels Coupled to Small-Bore Capillaries". Anal. Chem., 65:3313–3319 (1993).

Primary Examiner—Vincent P. McGraw
Attorney, Agent, or Firm—Testa, Hurwitz & Thibeault, LLP

[57] ABSTRACT

Disclosed is an apparatus for fluidic separation systems comprising a microfabricated conduit including a usefully long optical pathlength. The provision of a usefully long optical pathlength in the apparatus greatly improves the sensitivity of detection of separated analytes without compromising the resolving power of the apparatus.

39 Claims, 2 Drawing Sheets

MODULE FOR OPTICAL DETECTION IN MICROSCALE FLUIDIC ANALYSES

BACKGROUND OF THE INVENTION

This invention relates generally to the field of chemical analysis and more specifically to separation techniques such as electrophoresis and chromatography using fluidic conduits constructed by microfabrication techniques in planar substrates.

Electrophoresis and chromatography are well established techniques for separation and analysis of mixtures. Electrophoresis involves the migration of molecules in an electric field and their separation based on differences in mobility. Many different forms of electrophoresis have been developed to permit the separation of different classes of compounds. These forms include free zone electrophoresis, gel electrophoresis, isoelectric focusing, and isotachophoresis. Chromatography involves the interaction of molecules contained in a moving fluid stream with a usually stationary surface and their separation based on differential interaction of the molecules with the surface. Many forms of chromatography have been developed including ion exchange, affinity chromatography, and various types of adsorption chromatography.

There has been interest in using techniques developed originally for the fabrication of semiconductor electronic devices to construct microscale fluidic devices that can be used in chemical analysis. In general, this involves etching or laser ablating channels into the surface of a substrate such as silicon, glass or fused silica. A cover is bonded onto the substrate after channel formation resulting in enclosed channels which can be accessed through holes in the cover or the substrate.

For performing electrophoretic separations, several channel geometries have been used. They consist of a separation channel connecting two electrolyte reservoirs in which electrodes are incorporated. Side channels connecting with the separation channel can be used to introduce sample solution or for bringing reagents into the separation channel. The dimensions of the channels are kept small to limit power dissipation and to facilitate the removal of heat generated in the electrophoretic process. Typical dimensions are about 5 to 100 microns for the channel depth and about 10 to 1000 microns for the channel width.

A means for detecting the separated sample components is required. This can be performed in several ways. Electrical measurements based on conductance or electrochemical reactions can be performed with electrodes incorporated into the channel structure. Conductivity measurements can detect ionic species. Electrochemical measurements are generally limited to electroactive compounds. Optical measurements which can be performed in these systems include absorbance, fluorescence and chemiluminescence. Absorbance measurements are quite general and have moderate sensitivity. Fluorescence and chemiluminescence offer very high sensitivity but are applicable only to those compounds which are fluorescent or can produce chemiluminescence. For absorbance detection and to some extent the other optical detection methods a critical parameter is the optical path length. This is the length of the sample containing solution through which the measuring light beam travels. In accordance with Beers Law, the absorbance signal is proportional to the path length. Fluorescence intensity is also proportional to the path length of the excitation light beam for dilute samples.

An object of this invention is to provide an apparatus having microfabricated channels in a planar substrate that can analyze microvolumes of a sample fluid and produce analytical results rapidly. Another object is to provide an easily mass produced, disposable, small (e.g., less than 5 μl volume) apparatus useful in rapid, automated analyses of analytes in a range of biological and other applications. It is a further object of the invention to provide a family of such apparatus that individually can be used to implement a range of assays wherein the information indicative of the assay results is obtained by measuring an optical parameter of the sample fluid within a linear passage of the apparatus. Another object of the invention is to increase the path length of the flow cell without compromising the resolving power of the apparatus in order to provide for improved optical detection of the separated analytes. These and other objects and features of the invention will be apparent from the description, drawings and claims which follow.

SUMMARY OF THE INVENTION

The invention disclosed herein provides an apparatus having a usefully long optical path length for optical detection of analytes separated in fluidic separation systems. The apparatus includes a fluidic conduit comprising channels and a linear passage that are microfabricated in a planar substrate. In accordance with the invention the full thickness of the substrate, which can be a millimeter or more, is utilized for the optical path. The fluidic conduit is constructed by microfabricating a channel on both faces of the substrate and connecting the channels on opposing surfaces of the substrate with a linear passage through the substrate. In this way a fluidic conduit is formed that passes from one side of the substrate to the other. The portion of the fluidic conduit formed by the linear passage through the substrate is used as the detection region and thus the available optical pathlength is defined by the thickness of the substrate rather than the depth of the channel.

The apparatus may be constructed by microfabricating channels and linear passage(s) upon a single substrate, and the channels enclosed by separate covers (which may comprise substrates) that are placed in contact with either surface of the substrate. The apparatus may also be constructed by the combination of three stacked substrates which have been sandwiched together into a single unit. The second substrate, or middle substrate, will be microfabricated to define the linear passage(s). The first and second substrates can be microfabricated to define at least a first channel. The first channel can be microfabricated on the surface of the first substrate and enclosed by the second substrate. The first channel also can be microfabricated on the surface of the second substrate and enclosed by the first substrate. The first channel also can be partially microfabricated into each of the first and second substrates and enclosed by the mating of the substrate surfaces upon sandwiching the substrates into the complete unit. Likewise, the second and third substrates can be microfabricated to contain a channel which is disposed on only one of the substrates and enclosed by the other substrate, or is distributed between the substrates. The enclosed channels can be accessed via a port or hole in the cover or, alternatively, in the first substrate. Channels which are disposed between the second and third substrates can be accessed through a hole or port in the third substrate when desired. If a channel extends to an edge of the substrate or to the combination of three substrates, then it may be accessed from the end. Other approaches to accessing the channels also may be used.

In an effort to avoid duplication of description, the following descriptions of separate embodiments of the apparatus will be presented with reference to an apparatus in which each channel and linear passage is disposed upon a single substrate. As will be apparent to one of ordinary skill in the art, the precise number of channels disposed upon a substrate, and the geometry of the channels disposed upon a substrate can be altered to suit a particular apparatus, and the following descriptions provide a list of preferred channel configurations.

In one embodiment, the apparatus of the invention includes a substrate having a channel disposed on one surface and a linear passage through the substrate connecting the first channel with the second surface. The channel may be enclosed by adhering a cover to the first surface of the substrate. The channel may also be enclosed by any other method which is known in the art, for example by filling the channel with a liquid, depositing a coating upon the surface of the substrate and removing the liquid from the channel.

In one embodiment, the apparatus of the invention includes a substrate having a channel disposed upon one surface, a channel disposed on the opposing surface, and a linear passage through the substrate connecting the first channel with the second channel. The channels may be enclosed by adhering a cover to each surface of the substrate, upon which a channel is disposed, or by any other method which is known in the art.

In another embodiment, the apparatus of the invention includes a substrate having two non-contiguous channels disposed upon a first surface, and a channel disposed on an opposing second surface, and two passages, one of which is a linear passage, through the substrate. One passage connects the first non-contiguous channel with the channel on the second surface, and the other passage connects the channel on the second surface with the second non-contiguous channel on the first surface.

A multiplicity of fluidic conduits can be arranged in parallel on a substrate using any of the above apparatus designs. The fabrication of a multiplicity of fluidic conduits in a single substrate allows a panel of assays to be conducted simultaneously.

A substrate, or the middle substrate of three substrates, is typically fused silica, silicon, glass or an organic polymer. A cover, or the first and third substrates of three stacked substrates, is typically an optically transparent material, or a material which has optically transparent portions in the area enclosing the junction of a channel to the transecting linear passage. Suitable optically transparent covers include glass, fused silica, and sapphire.

In an assay, a fluid sample which is to be analyzed for one or more analytes is delivered to an inlet port of the apparatus and at least a portion of the sample is allowed to enter a microfabricated separation channel, thereby subjecting the sample to electrophoresis, chromatography or affinity interaction, resulting in the separation of the sample components. As would be understood by one of skill in the art, reagents can be added to the sample before or after the separation through side ports to cause the formation of detectable species. The separation channel is in fluid communication with a linear passage through the substrate. The presence of a suspected analyte in the sample is determined by optical detection of a moiety indicative of the analyte in an optical path which is coaxial with the linear passage through the substrate.

Analytes which are detectable by fluorescence, light absorption or chemiluminescence are readily detected in the apparatus. Useful optical detectors include fluorescent, infrared, UV or visible light detectors. The sensor portion of an optical detector will be positioned with respect to the axis of the linear passage such that the optical parameters of the analytes within the linear passage can be measured.

The apparatus of the invention may be utilized to rapidly detect and/or quantitate one or a plurality of analytes in a single or plural separate fluid samples. The apparatus can be adapted easily for automated analysis, and requires only very small quantities of reagents. The apparatus can be utilized with essentially any assay method which has optically detectable results, for example various components in a biological fluid sample may be detected, such as enzymatic, hormonal, genetic, viral or other components. The design of the apparatus allows rapid, standardized, mass production of the apparatus. The apparatus may be readily sterilized prior to an assay, thus allowing use in microbiological assays and other procedures requiring clean environments. Assays may be completed rapidly and at the conclusion of the assay, the apparatus can be discarded, which advantageously prevents contamination between samples, entombs potentially hazardous material, produces only microvolumes of waste fluid for disposal, and provides an inexpensive, microsample analysis.

The invention will be understood further from the following drawings, description and claims.

BRIEF DESCRIPTION OF THE DRAWINGS

FIG. 4 also depicts the excitation of the sample contained within each of the plurality of linear passages with fluorescent light focused transversely through the sample in the direction of the dotted arrow. Detectors are shown coaxially positioned with each linear passage, such detectors will be useful for detecting the light emitted by fluorescently excited sample constituents.

Each figure is drawn using an exaggerated scale in order to clearly depict the microfabricated fluidic conduit of the apparatus. Like reference characters in the respective drawn figures indicate corresponding parts.

DETAILED DESCRIPTION OF THE INVENTION

Figure 1:
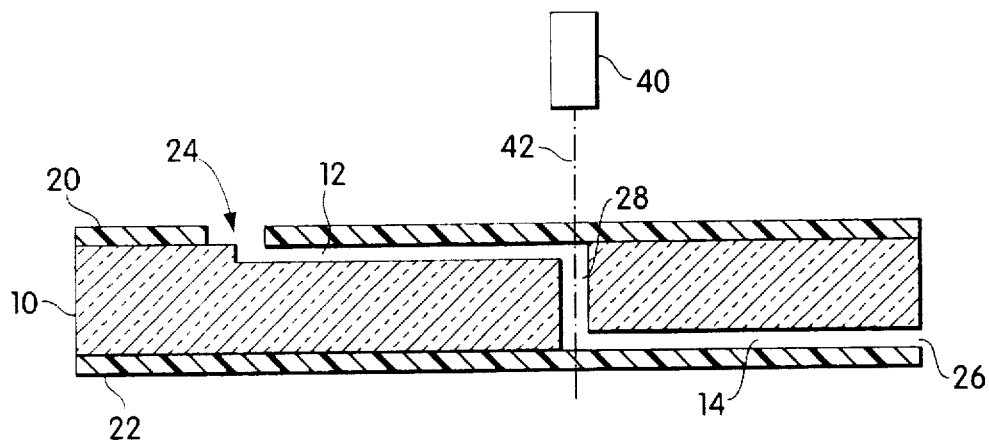
FIG. 1 is a schematic longitudinal cross-sectional view of an apparatus of the invention having a fluidic conduit comprising two channels and a linear passage. A detector is shown coaxially positioned with the linear passage.

The invention provides an apparatus, a method of manufacturing the apparatus and methods of detecting an analyte using the apparatus.

Generally, as disclosed herein, the apparatus of the invention comprises a substrate containing the microfabricated channel system. The apparatus can be fabricated from silicon and other solid substrates using established micromachining methods, or by molding polymeric materials, including polystyrene, polyacrylate and polycarbonate. The substrate, or the middle substrate of a stacked three substrate apparatus, is preferably at least about 50 microns thick, and can be about 5000 microns thick or greater. More preferably, the substrate is about 400 microns to about 2000 microns thick.

A cover, or the first and third substrates of a three substrate apparatus, is typically an optically transparent material, or a material which has optically transparent portions in the area enclosing the junction of a channel to the transecting linear passage. Suitable optically transparent materials include glass, fused silica, and sapphire. A material will be at least about 10 microns thick and can be several thousand microns thick (about 5000 microns) depending upon the design of the apparatus. Preferably, a cover, or the first and third substrates, will be about 400 microns to 1000 microns thick. A cover may also comprise a sealant layer which is deposited upon the surface of the substrate after microfabrication of the conduit. For example, the microfabricated conduit could be filled with a removable material, e.g., a water or oil based liquid, the sealant layer applied to the substrate surface and then the material in the conduit removed.

The channels and linear passage have preferred internal dimensions of between about 0.1 microns and about 1000 microns. The channel widths are more preferably between about 10 microns and about 1000 microns. The channel depths are more preferably between about 5 microns and about 100 microns. The linear passage preferably has an inner diameter of about 5 microns to about 1000 microns.

The channels and linear passage in cross-section taken through the thickness of the substrate may be triangular, truncated conical, square, rectangular, circular, or any other shape. The fluidic conduits of the apparatus typically are designed on a scale suitable to analyze microvolumes (<about 5 µl) of sample introduced into the flow system through an inlet port defined, e.g., by a hole communicating with the flow system through the substrate or through a cover. Analyte present in very low concentrations (e.g., approximately nanogram quantities) in microvolumes of a sample fluid can be rapidly analyzed (e.g., <about 10 minutes).

The apparatus can be formed by microfabricating each channel and linear passage in a single substrate and then enclosing the channels and linear passage with covers or by any other suitable means for sealing the fluidic conduit. The apparatus also can be formed from three stacked substrates which are sandwiched together. In such an apparatus the first and second substrates define the first channel (and any non-contiguous third channel), the second substrate defines the linear passage(s), and the second and third substrates define the second channel. The first substrate may also contain holes or ports for providing access to the channel(s) when required. As will be generally understood by those of ordinary skill in the art, either of the first or second substrate, or second and third substrates, can substantially define the channel and the other substrate can substantially enclose the channel. A channel may also be distributed between each of the substrates such that a percentage of the channel is defined by each of the substrates when sandwiched together. The term "substantially define a channel" is used herein to designate that a channel has been microfabricated on the surface of the substrate. The term "substantially enclose a channel" is used herein to designate that the substrate is primarily acting to seal, or cover, the channel which has been microfabricated on the opposing substrate.

In the first two embodiments described below, FIGS. 1 and 2, the apparatus is described as a single substrate the channels and linear passage(s) of which are enclosed by covers. As would be generally understood, the described channel configurations also can be accomplished by the formation of an apparatus composed of three substrates which have been sandwiched together. In the third embodiment described below, FIG. 3, the apparatus is described as formed from three substrates which have been sandwiched together. In this apparatus, the passages have been microfabricated in the second substrate and the channels have been microfabricated on the first and third substrates. Assembly of the substrates into a sandwich results in enclosing the channels and formation of the complete fluidic conduit through the three substrates.

In one embodiment, illustrated in FIG. 1, the apparatus may include a substrate 10 microfabricated with a fluidic conduit, comprising channels 12, 14 on either side of the substrate and a linear passage 28 which connects the channels through the substrate, and covers 20, 22 which enclose the fluidic conduit. A port 24, can be provided through a hole in the cover 20, or alternatively, as an opening 26, where the substrate 10 and the cover 22 end. An optical detector 40 is positioned in the central axis of the linear passage, shown as dotted line 42, to measure the optical properties of an analyte within the linear passage 28. The length and depth of each channel and linear passage, and the size of each port or opening is shown using an expanded scale in the figures in order to distinctly depict the features of the apparatus. As will be generally understood, the second channel 14 may be missing entirely or may be significantly shorter than the first channel. When present the second channel need only be of sufficient length such that the sample is directed away from the linear passage. This allows an accurate optical measurement to be made of any analyte which is within the linear passage. Structures other than a second channel may also be used to direct the sample away from the linear passage. For example, as an alternative to providing a second channel 14 to direct the sample away from the linear passage, the apparatus can be mounted at an angle to the horizontal plane such that the force of gravity will cause the sample to drain away from the linear passage.

Figure 2:
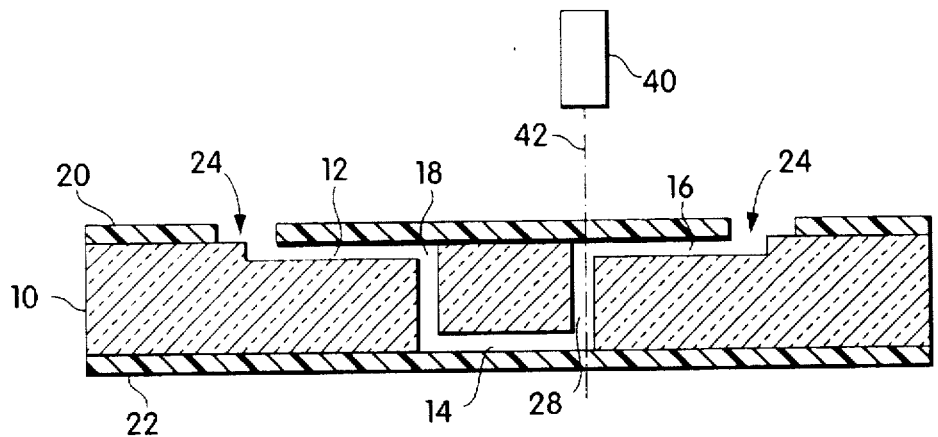
FIG. 2 is a schematic longitudinal cross-sectional view of an apparatus of the invention having a fluidic conduit comprising three channels and two linear passages. A detector is shown coaxially positioned with the linear passage.

In another embodiment, illustrated in FIG. 2, the apparatus may include a substrate 10 microfabricated with a fluidic conduit, comprising non-contiguous channels 12, 16 disposed on one side of the substrate and channel 14 disposed on the opposite side of the substrate. Linear passage 18 connects the first channel 12 with the second channel 14 and linear passage 28 connects the second channel 14 with the third channel 16. When the channels 12, 14, 16, are enclosed with covers 20, 22, as depicted, ports 24 can be provided in the cover 20 which encloses the first channel 12 and the third channel 16. An optical detector 40 is positioned in the central axis of the linear passage, shown as dotted line 42, to measure the optical properties of an analyte within the linear passage 28.

Figure 3:
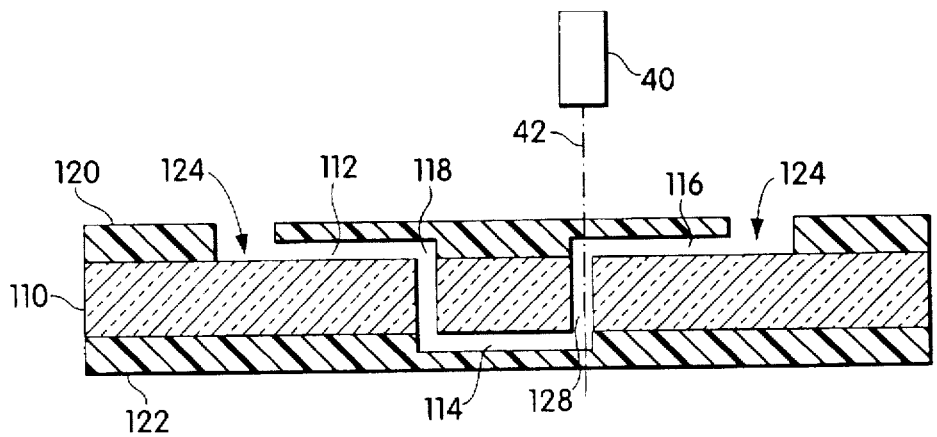
FIG. 3 is a schematic longitudinal cross-sectional view of an apparatus of the invention having a fluidic conduit comprising three channels disposed on the first and third substrates and two linear passages disposed within the second substrate. A detector is shown coaxially positioned with the linear passage.

In another embodiment, illustrated in FIG. 3, the apparatus may comprise a fluidic conduit in which a substrate 110 having linear passages 118, 128, and substrates 120, 122 having channels 112, 114, 116 are sealed together into a sandwich. Ports 124 may be provided in substrate 120 to allow access to the first channel 112 and third channel 116. An optical detector 40 is positioned coaxially with the central axis of the linear passage, shown as dotted line 42, to measure the optical properties of an analyte within the linear passage 128. The apparatus of the invention also can be microfabricated such that at least one channel is disposed on substrate 110 and an additional channel or channels are disposed substrates 120 and 122, as discussed above.

It is clear that many configurations of the apparatus are possible and will be apparent from the description or from the practice of the invention.

Optical detection of analytes within the linear passage can be accomplished by positioning a detector at either end of the linear passage. Positioning of the detector at an end of the long central axis of the linear passage provides for a long optical path length, which greatly improves the sensitivity of detection of an analyte present in the fluidic conduit. Importantly, the design of linear passage results in an increased volume of sample which is measured by optical detection without compromising the resolving capability of the fluidic conduit.

Figure 4:
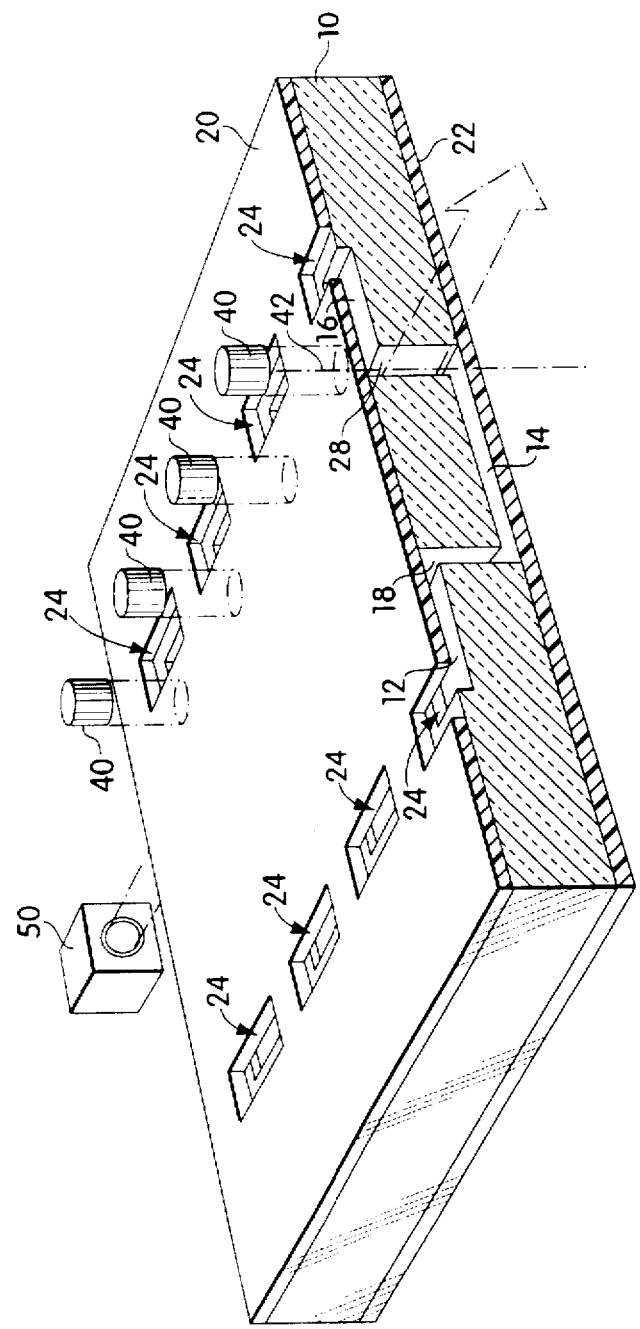
FIG. 4 is a perspective view of an apparatus fabricated to contain a plurality of fluidic conduits.

FIG. 4 shows an apparatus with multiple fluidic conduits comprised of channels 12, 14, 16 each of which is configured for long path length detection through the central axis of a linear passage 18 or 28. Each fluidic conduit is provided with ports 24 for accessing the enclosed channels.

FIG. 4 also shows the apparatus of the invention used for fluorescence detection. In FIG. 4 the excitation light, emitted from a fluorescent light emitter 50, enters through the edge of the substrate 10, which necessarily must be transparent, and illuminates each linear passage 28 in a plurality of fluidic conduits. An optical detector 40 is positioned coaxially with each linear passage 28 such that the detector 40 can detect the emission from the sample within the linear passages 28. The emission from an analyte can be measured using a detector positioned at either side of the microfabricated channel system, relative to the central axis 42 of the linear passage 28. The configuration of the apparatus provides both a long optical path length, the linear passage 28, and also provides for orthogonality of the direction of excitation and emission which is desirable from the point of view of minimizing scatter of the excitation light in the direction in which emitted light is measured.

The apparatus of the invention having a single or multiple fluidic conduits can be designed and fabricated in large quantities from a solid substrate material. They also can be easily sterilized. Silicon is a preferred substrate material because of the well-developed technology permitting its precise and efficient fabrication, but other materials may be used including glass, fused silica and cast or molded organic polymers, including polystyrene, polyacrylate, and polycarbonate. The channels, linear passage(s) and other functional elements, such as a sample inlet or ports, may be fabricated inexpensively from a silicon substrate by any of a variety of micromachining methods known to those skilled in the art. The micromachining methods available include film deposition processes such as spin coating and chemical vapor deposition, laser fabrication or photolithographic techniques such as UV or X-ray processes, or etching methods which may be performed by either wet chemical processes or plasma processes. (See, e.g., Manz et al., *Trends in Analytical Chemistry*, 10: 144–149 (1991)). Microfabricated channels of varying widths and depths can be fabricated for use in the apparatus.

In one preferred embodiment, an apparatus having the design depicted in FIG. 2 is manufactured using the following steps. Both positive and negative photoresist techniques are equally useful, and the following example briefly describes the use of a positive photoresist technique. A fused silica substrate is first coated with a 450 angstrom thick layer of chrome on each side by sputtering or evaporation. Photoresist is spun onto both sides of the substrate. A photomask, which provides the template for the two non-contiguous channels, is placed against the first surface of the substrate. The photomask covered substrate is then exposed to UV light, which causes a chemical reaction in the exposed photoresist and renders the exposed photoresist sensitive to photoresist developer. A photomask which provides the template for the single channel is placed against the second surface and the photomask covered substrate is exposed to UV light. The substrate is then placed in photoresist developer which dissolves the UV reacted photoresist and exposes the underlying chrome layer. The developed substrate is then placed in a bath of chrome etchant which dissolves the chrome where the photoresist has been removed and exposes the surface of the substrate. The substrate is then placed in a bath of buffered hydrofluoric acid, which etches the exposed substrate. The chrome layer allows deeper etching of the substrate than if photoresist alone is employed and also serves to prevent exposure of the photoresist on one side of the substrate by UV light transmitted through the substrate during the exposure of the other side. Thus it is not necessary to separately process each surface of the substrate. Due to the amorphous structure of fused silica, the etching is isotropic thus resulting in etching in a direction under the remaining chrome and photoresist, and the formation of channels which are wider than they are deep. The use of silicon, quartz or other crystalline substrate can result in the formation of channels having a more nearly equal aspect ratio of depth and width.

After channel formation, a hole (the linear passage) is formed through the substrate connecting the channels on opposite surfaces. The hole can be formed by techniques that allow precise micron sized holes to be machined. Laser drilling is one such technique. Micro sand blasting or a very small water jet are other techniques for making small holes that may serve this purpose.

The channels on the opposing surfaces must be in close registration in order for the linear passage to effectively connect the channels. Close registration can be achieved by careful production of paired photomasks for either surface of the substrate and uniform treatment of each side of the substrate during UV exposure, photoresist developing, and etching.

In another preferred embodiment, channels can be etched on separate covers using the method described above and the linear passage can be microfabricated in the substrate. The three components can be aligned to register the linear passage(s) with the channels and the components sealed together to form the apparatus having a fluidic conduit.

In non-transparent substrates, it may be advantageous to form channels on one side of the substrate and then form the through hole. The through hole can then be used to register the channels to be formed on the other side, either lithographically or by laser ablation. One advantage of a non-transparent substrate is that the optical detection region formed by the through hole is self masking (i.e. light can only pass through the hole).

A substrate containing microfabricated channels and linear passage(s) may be covered and sealed, e.g., anodically bonded, with a thin glass cover. Other clear or opaque cover materials may be used, and the cover need only be clear in the region covering the linear passage. A mask could be provided in a transparent substrate by depositing and patterning an opaque material on the cover layer.

An apparatus which is a sandwich of three stacked substrates can be sealed into a unit by any available technique, i.e. anodic bonding. The middle substrate of the apparatus can be any suitable material as described above, and selection of a non-optically transparent material will result in self-masking the linear passage. The outer two substrates can be completely optically transparent and need to only incorporate optically transparent portions in the region on either side of the linear passage.

In a preferred embodiment, the second substrate is composed of silicon, fused silica or glass. Optically transparent first and third substrates (or covers) are provided which are composed of fused silica or glass. These materials can be thermally bonded together without the use of adhesives or sealants. The bonding process involves thorough cleaning of the substrates, bringing the pieces into contact in a clean environment (low in particulates), and elevating the temperature to cause bond formation. A potential can be applied to the pieces, after bringing them into contact, in order to encourage bonding.

In one currently preferred method of fabrication, the first second and third substrates are composed of fused silica. The substrates are cleaned and activated in dilute $NH_4OH/H_2O_2$ solution and then transferred to a bath of filtered, deionized water where they are brought into contact. Once in contact, the pieces are removed from the bath and placed into an oven. The temperature is raised at 0.2° C./min. to 200° C. and held for at least 4 hours to drive out residual water. Thereafter the joined pieces are placed in a furnace. The temperature is raised at 2° C./min. to 200° C., held for 2 hours and then raised at 2° C./min. to 1000° C. and held for 6 hours. The furnace is then turned off and allowed to cool to room temperature. This method yields assemblies with substrates and covers bonded into an integrated unit.

The capacity of the fluidic conduits in the apparatus is very small, and therefore the amount of fluid required for an analysis is low. For example, in a 1 cm×1 cm silicon substrate, having on its surface an array of fluidic conduits which are 10 microns deep and 1 cm ($10^4$ microns) long, the volume of each fluidic conduit is $10^{-3}$ μl. The total volume of 500 of such fluidic conduits, which could be arrayed on a single substrate, is 0.5 μl. The low volume of the fluidic conduits allows assays to be performed on very small amounts of a liquid sample (<0.5 μl). The fluidic conduits may be fabricated with microliter volumes, or alternatively with nanoliter volumes or less, which advantageously limits the amount of sample, buffer or other fluids required for an analysis. Thus, an important consequence and advantage of employing an apparatus having fluidic conduits with sub-millimeter (micron) dimensions is that very small scale analyses can be performed.

The sample or reactant volumes may be introduced by any of the methods employed in capillary electrophoretic and chromatography systems, including hydrodynamic, electrokinetic, vacuum, injection port, and syringe methods. Furthermore, the systems can be readily automated for injection with commercially available autoinjectors.

The apparatus can be used in combination with an appliance for delivering and receiving fluids to and from the apparatus which incorporates a nesting site for holding the apparatus and mates an input port on the apparatus with a flow line in the appliance, thus facilitating automation of sample analysis. In general the apparatus will be disposed in an appliance in a horizontal plane, samples will be delivered to an inlet, a force (e.g., electric field, a pump, or capillary action) will be utilized to transport the sample through the channels and linear passage, and an optical detector will be situated to detect the presence of an analyte as it passes through a linear passage. Alternatively, the apparatus may be disposed, e.g., in an appliance, at an angle with respect to a horizontal plane, to provide an incline for the travel of the sample fluid away from the exit of the linear passage without the disposition of a second channel upon the second surface of the substrate. Placement of such an apparatus at an angle with respect to the horizontal plane would allow clear detection through the linear passage by an optical detector without the need for a second channel or a second cover.

Any conventional method of detection may be used in combination with the apparatus of the invention. A detection method may be chosen which allows for detection of any physical property of a chemical species. Preferred detection methods include, but are not limited to, absorbance of infrared, ultraviolet or visible light radiation, chemiluminescence and fluorescence. Detection of analytes which have been separated by electrophoresis, supercritical fluid chromatography, or liquid chromatography may occur at a discrete position along the length of the channel, preferably by imaging along the axis of the linear passage of the apparatus. Use of optical detectors to detect analytes in the linear passage are compatible for use in combination with detectors which operate by directly sensing separated sample constituents as they exit the apparatus. Examples of such detectors which detect analytes after exit from the fluidic conduit include mass spectrometric detectors and electrochemical detectors.

A large number of assay protocols known in the art may be exploited with the microfabricated fluidic conduit system of the invention. Assays for the detection of an analyte utilizing isoelectric focusing techniques and specific binding reactions are disclosed in U.S. Pat. No. 5,376,249, issued Dec. 27, 1994, and in U.S. Ser. No. 08/358,192, filed Dec. 16, 1994 the disclosures of which are specifically incorporated herein by reference. The apparatus may also be adapted for use with the rapid flowthrough immunodetection assay disclosed in U.S. Ser. No. 08/196,996, filed Feb. 11, 1994, the disclosure of which is specifically incorporated herein by reference. The apparatus may also be used for electrophoretically mediated chemical analysis as disclosed in U.S. Ser. No. 08/386,224, filed Feb. 9, 1995, the disclosure of which is specifically incorporated herein by reference.

As used herein, the term "analyte" is intended to mean any substance susceptible to optical detection using the instant apparatus, and any substance which can be bound to one or more binding partners which render the complex detectable by optical detection in the instant apparatus. A "binding partner", as used herein, is any biochemical or chemical moiety which has an ability to interact specifically with, and bind with, a corresponding analyte. Currently preferred analytes and binding partners include chemical and biochemical moieties. For example, analytes and binding partners suitable for analysis in the instant invention include, but are not limited to, the following biochemical and chemical moieties: proteins, peptides, nucleic acids, peptide hormones, non-peptide hormones, drugs of abuse, environmental pollutants, pharmaceuticals, microbial antigens, viral antigens, carbohydrates, polyclonal antibodies, monoclonal antibodies, anti-idiotypic antibodies, antibody fragments, enzyme substrates, enzyme inhibitors, biotin, and receptors. It will be further understood that biochemical or chemical substances which can be rendered amenable to complex formation, i.e., can be manipulated or modified to bind with at least one binding partner or two different binding partners, are considered suitable for detection in the instant apparatus.

As used herein, the term "sample" is intended to mean any specimen to be analyzed for an analyte of interest. Currently preferred samples for analysis include, but are not limited to, any biological or environmental specimen suspected to contain an analyte of interest. The instant apparatus is suitable for detection of analytes in samples of body fluids including, but not limited to: blood, serum, plasma, urine, cerebrospinal fluid, saliva, sweat, semen, vaginal fluid, amniotic fluid, and ascites fluid. With respect to analytes which are environmental pollutants, they can be detected in fluids such as, but not limited to, rain water, ocean water, and sewer water.

The invention may be embodied in other specific forms. What is claimed is:

1. Apparatus for analysis of a fluid in a conduit, said apparatus comprising:
   a) stacked first, second and third substrates each having opposing first and second surfaces,
   b) a first microfabricated channel having a depth between about 5 microns and about 100 microns, defined by the interface of the first substrate and the second substrate,
   c) a second microfabricated channel having a depth between about 5 microns and about 100 microns, defined by the interface of the second substrate and the third substrate, and
   d) a first linear passage through the second substrate, said linear passage having a central axis, connecting the first channel with the second channel.

2. The apparatus of claim 1 further comprising:
   e) a third channel defined by the interface between the second surface of the first substrate and the first surface of the second substrate, said third channel being non-contiguous with said first channel, and
   f) a second passage through the second substrate, connecting the second channel with the third channel.

3. The apparatus of claim 1 wherein said first substrate and said third substrate comprise optically transparent substrates.

4. The apparatus of claim 1 wherein said first substrate and said second substrate comprise substrates having an optically transparent portion disposed on either end of said first linear passage.

5. The apparatus of claim 1 wherein the distance between said first and second surfaces of said second substrate is at least 50 microns.

6. The apparatus of claim 1 wherein the distance between said first and second surfaces of said second substrate is between 50 microns and 5000 microns.

7. The apparatus of claim 1 wherein the distance between said first and second surfaces of said second substrate is about 400 microns to 2000 microns.

8. The apparatus of claim 1 wherein the surfaces of said substrates are substantially flat.

9. The apparatus of claim 1 wherein at least one of the first substrate and the third substrate comprise a sealant layer disposed upon the first and second surfaces of said second substrate.

10. The apparatus of claim 1 wherein the distance between the first and second surfaces of the first substrate and the third substrate is at least about 10 microns.

11. The apparatus of claim 1 wherein the distance between the first and second surfaces of the first substrate and the third substrate is between about 10 and 5000 microns.

12. The apparatus of claim 1 wherein the distance between the first and second surfaces of the first substrate and the third substrate is about 400 to 1000 microns.

13. The apparatus of claim 1 further comprising:
   e) an optical detector for detecting the presence of an analyte of a fluid in said linear passage, said optical detector positioned along an optical path substantially coaxial with the central axis of said linear passage.

14. Apparatus for analysis of a fluid in a conduit, said apparatus comprising:
   a) a substrate having opposing first and second surfaces,
   b) a first microfabricated channel having a depth between about 5 microns and about 100 microns, disposed on the first surface,
   c) a first linear passage through the substrate, connecting the first channel with the second surface, said linear passage having a central axis, and
   d) an optical detector positioned along an optical path substantially coaxial with the central axis of the linear passage to detect an optical property of an analyte component of the fluid.

15. The apparatus of claim 14 further comprising:
   e) a first cover on the first surface of the substrate.

16. The apparatus of claim 14 further comprising an optically transparent member disposed on an end of said first linear passage.

17. The apparatus of claim 14 further comprising:
   e) a second channel disposed on the second surface, said linear passage connecting the first channel with the second channel.

18. The apparatus of claim 17 further comprising:
   e) a third channel disposed on the first surface, said third channel being non-contiguous with said first channel, and
   f) a second passage through the substrate, connecting the second channel with the third channel.

19. The apparatus of claims 17 or 18 further comprising
   g) a first cover on the first surface of the substrate, and
   h) a second cover on the second surface of the substrate.

20. The apparatus of claim 17 wherein said first and second cover comprise an optically transparent member disposed on both ends of said first linear passage.

21. The apparatus of claim 14 wherein the distance between the first and second surfaces of the substrate is at least about 10 microns.

22. The apparatus of claim 14 wherein the distance between the first and second surfaces of the substrate is between about 10 and 5000 microns.

23. The apparatus of claim 14 wherein the distance between the first and second surfaces of the substrate is about 400 to 1000 microns.

24. The apparatus of claims 13 or 14 wherein said optical detector detects fluorescence.

25. The apparatus of claims 13 or 14 wherein said optical detector detects light absorbance.

26. The apparatus of claims 13 or 14 wherein said optical detector detects chemiluminescence.

27. The apparatus of claims 1 or 14 wherein said substrate comprises glass, fused silica, silicon, quartz, or an organic polymer.

28. The apparatus of claims 1 or 14 wherein said apparatus includes a multiplicity of conduits disposed within said substrate.

29. The apparatus of claims 1 or 14 wherein, within at least a portion of said channel, the channel width and channel depth are between 0.1 microns and 1000 microns.

30. The apparatus of claims 1 or 14 wherein the channel width is 10 microns to 1000 microns.

31. Method of manufacture of a conduit which includes an optical flow path comprising the steps of:
   a) providing a planar substrate having opposing first and second surfaces,
   b) forming a first channel on the first surface using microfabrication methods,
   c) forming a second channel on the second surface using microfabrication methods,
   d) forming a first linear passage through the substrate, connecting the first channel with the second channel.

32. The method of claim 31 wherein said method further comprises the steps of:

e) sealing the first surface, and f) sealing the second surface.

33. The method of claim 31 wherein said sealing step comprises covering said first and second channels with an optically transparent composition.

34. The method of claim 31 wherein said sealing step covering said first and second channels with a composition having an optically transparent portion situated at the site where the linear passage connects said first and second channels.

35. The method of claim 31 wherein said method further comprises the steps of:

e) forming a third channel on the second surface, said third channel being non-contiguous with said second channel, and f) forming a second passage through the substrate, connecting the first channel with the third channel.

36. The method of claim 35 wherein said method further comprises the steps of:

g) sealing the first surface, and h) sealing the second surface.

37. The method of claim 35 wherein said sealing step comprises covering said first and second channels with an optically transparent composition.

38. The method of claim 35 wherein said sealing step covering said first and second channels with a composition having an optically transparent portion situated at the site where the linear passage connects said first and second channels.

39. An apparatus for analysis of fluid in a conduit, said apparatus comprising:

a) stacked first, second and third substrates each having opposing first and second surfaces;

b) a first channel defined by the interface of the first substrate and the second substrate;

c) a second channel defined by the interface of the second substrate and the third substrate;

d) a linear passage through the second substrate, said linear passage having a central axis, and connecting each first channel with a corresponding second channel; and e) a source of excitation light located such that said excitation light is directed through said second substrate orthogonally to said linear passage, said second substrate being transparent to said excitation light.

* * * * *